United States Patent [19]

Baumann et al.

[11] 4,268,506
[45] May 19, 1981

[54] THIENYLMETHYL-THIOPHOSPHORIC ACID ESTERS

[75] Inventors: Annegrit Baumann, Mannheim; Heinrich Adolphi, Limburgerhof, both of Fed. Rep. of Germany

[73] Assignee: BASF Aktiengesellschaft, Federal Republic of Germany

[21] Appl. No.: 54,862

[22] Filed: Jul. 5, 1979

[51] Int. Cl.³ .................. A61K 31/38; C07D 333/14
[52] U.S. Cl. ........................................ 424/202; 549/6; 549/8
[58] Field of Search ................. 549/6, 8; 424/202

[56] References Cited

U.S. PATENT DOCUMENTS

| | | | |
|---|---|---|---|
| 2,769,013 | 10/1956 | Lowenstein-Lom | 549/6 |
| 3,205,238 | 9/1965 | Godfrey | 549/8 |
| 3,242,046 | 3/1966 | Godfrey | 549/8 X |
| 3,449,366 | 6/1969 | Lies | 549/6 |
| 4,128,562 | 12/1978 | Perronnet | 549/8 |

Primary Examiner—John D. Randolph
Attorney, Agent, or Firm—Keil & Witherspoon

[57] ABSTRACT

New thienylmethyl-thiophosphoric acid esters of the formula

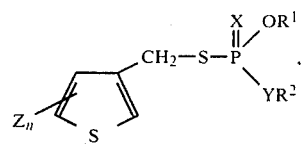

where $R^1$ denotes methyl or ethyl, $R^2$ denotes linear or branched alkyl of a maximum of 5 carbon atoms, X denotes oxygen or sulfur, Y denotes sulfur or —NH—, Z denotes halogen, and n denotes one of the integers 0, 1, 2 and 3, which are effective against pests, especially insects, Arachnida and Nemathelminthes, and pesticides containing these compounds as active ingredients.

5 Claims, No Drawings

THIENYLMETHYL-THIOPHOSPHORIC ACID ESTERS

The present invention relates to new thienylmethyl-thiophosphoric acid esters, a process for their manufacture, pesticides containing these phosphoric acid esters as active ingredients, and a process for combating pests with these active ingredients.

Insecticidally active O,O-dialkyl-S-thienylmethyl-thiophosphoric acid esters are disclosed in U.S. Pat. Nos. 3,205,238; the thienyl radical may either be unsubstituted or bear up to two halogen substituents.

We have now found that thienylmethyl-thiophosphoric acid esters of the formula

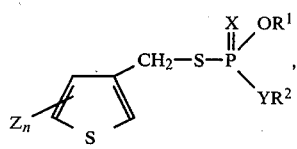

where $R^1$ denotes methyl or ethyl, $R^2$ denotes linear or branched alkyl of a maximum of 5 carbon atoms, X denotes oxygen or sulfur, Y denotes sulfur or —NH—, Z denotes halogen, and n denotes one of the integers 0, 1, 2 and 3, have an action superior to that of the prior art O,O-dialkyl-S-thienylmethyl-thiophosphoric acid esters. The compounds according to the invention are excellently suited for combating insect pests and pests from the Arachnida and Nemathelminthes classes.

In formula I, $R^1$ preferably denotes ethyl and $R^2$ linear or branched alkyl of a maximum of 5 carbon atoms, for example methyl, ethyl, propyl, butyl and pentyl, preferably propyl and butyl, and especially n-propyl. Z denotes halogen, preferably chlorine or bromine.

The thienylmethyl-thiophsophoric acid esters of the formula I are obtained by reaction of thiophene derivatives of the formula

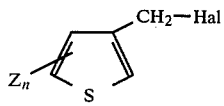

where Z and n have the above meanings and Hal denotes chlorine or bromine, with salts of the formula

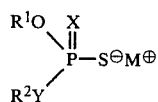

where $R^1$, $R^2$, X and Y have the above meanings and $M^\oplus$ denotes a substituted or unsubstituted ammonium ion, in the presence of a solvent or diluent.

Examples of suitable solvents or diluents are aromatic hydrocarbons such as benzene, toluene, xylenes and chlorobenzene; chlorinated or nitrated aliphatic hydrocarbons such as chloroform, 1,2-dichloroethane and nitromethane; aliphatic nitriles such as acetonitrile and propionitrile; acyclic and cyclic ethers such as diethyl ether and tetrahydrofuran; acyclic and cyclic ketones such as acetone, methyl ethyl ketone and cyclohexanone; and amides such as dimethylformamide. Water may also be used as solvent. Mixtures of these solvents may also be employed.

The reaction temperature may vary within a wide range. Generally, the temperature is from 10° to 100° C., preferably from 40° to 50° C., unless the boiling point of the solvent used sets an upper limit on the temperature.

To carry out the process, the thiophene derivatives of the formula II and the salts of the formula III are generally employed in equimolar amounts or advantageously with a 10% excess of the salts of the formula III. A larger excess offers no advantages. Generally, the thiophene derivative of the formula II and the solvent or diluent are placed in the reactor and the salt of the formula III, also either dissolved or suspended in solvent, is added. After a reaction period of several hours the solvent is removed and the remaining reaction batch is worked up by conventional methods. If necessary, the product obtained may subsequently be chromatographically purified.

The new compounds are obtained in the form of oils. They are characterized by their refractive index and elemental analysis.

The thiophene derivatives of the formula II may be obtained by reduction of a thiophene aldehyde of the formula

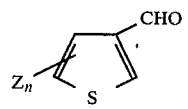

where Z and n have the above meanings, with a complex hydride, and reaction of the hydroxymethyl compound thus obtained with an inorganic acid chloride or bromide or with concentrated hydrochloric or hydrobromic acid.

Suitable complex hydrides are lithium hydrides and boric hydrides, e.g., $LiAlH_4$, $LiAl(OCH_3)_2H_2$, $NaBH_4$, $KBH_4$, or other hydrides having comparable reactivity. The preferred reducing agent is $NaBH_4$, as the reaction can then also be carried out in aqueous solvents. As a rule, equimolar amounts of hydride, based on thiophene aldehyde, are used.

The reduction is advantageously effected in an inert, or substantially inert, solvent. If $NaBH_4$ is used, lower alcohols such as methanol, ethanol, isopropanol or isobutanol, dialkyl ethers or cyclic ethers such as diethyl ether, methyl-tert-butyl ether, dioxane and tetrahydrofuran, or hydrocarbons are selected as solvents. Preferably, however, the reaction is carried out in water or in homogeneous or heterogeneous mixtures of water with one of the above solvents when $NaBH_4$ is the reducing agent.

The reduction is carried out at from $-10°$ to $+60°$ C., preferably from 0° to 40° C.

The product of the reaction may be worked up in conventional manner, e.g., by adding ethyl acetate, alcohols, water or mixtures of organic solvents with water. If $NaBH_4$ is the reducing agent, water is only added in such an amount that the 4-hydroxymethylthiophene which forms can be separated direct. Phase separation can be assisted by organic solvents.

To prepare the 4-chloromethylthiophene and 4-bromomethylthiophene compounds of the formula II, an inorganic acid chloride or acid bromide, e.g., $SOCl_2$, $SOBr_2$, $PCl_3$, $PBr_3$ and $POCl_3$, is added to the corresponding 4-hydroxymethylthiophenes advantageously suspended, emulsified or dissolved in an inert solvent. If desired, a catalyst, e.g., a tertiary organic amine, may be added.

Suitable inert solvents are particularly aliphatic halohydrocarbons such as $CH_2Cl_2$, $C_2H_4Cl_2$ and $CHCl_3$, saturated or unsaturated hydrocarbons such as n-pentane, n-hexane, and gasoline, and aromatic hydrocarbons such as toluene, xylenes and chlorobenzene. If possible, a solvent is not used, and a significant excess of the halogenating agent employed as solvent.

In another method, concentrated aqueous or nonaqueous hydrobromic or hydrochloric acid may be used. In this case, it is sufficient simply to react the 4-hydroxymethylthiophene by stirring with concentrated hydrochloric or hydrobromic acid at room temperature, to dilute with an inert solvent such as methylene chloride, and to isolate the 4-halomethylthiophene in the conventional manner.

The thiophene aldehydes of the formula IV where n denotes 1, 2 or 3 have been disclosed (Tetrahedron, 32, 1403–1406, 1976), and may be produced by halogenation of thiophene-3-aldehyde.

Preparation of 2,3-dichloro-4-chloromethylthiophene 300 ml of isopropanol, 300 ml of water and 200 g of 2,3-dichlorothiophene-4-aldehyde are placed in a 2 liter flask; over a period of 45 minutes, 16 g of sodium borohydride is added in portions. The reaction is exothermic and is cooled to take place at from 35° to 40° C. Subsequently, the two-phase mixture is stirred for 30 minutes at this temperature and then 300 ml of water and 500 ml of dichloromethane are added. After the phases have been separated, the aqueous phase is extracted twice with 250 ml of dichloromethane. The organic phases are washed with 250 ml of water and concentrated. The oily residue is taken up in cyclohexane; there is obtained 182 g (87.3% of theory) of crystalline 2,3-dichloro-4-hydroxymethylthiophene, m.p.: 63° to 65° C.

A mixtures of 357 g of thionyl chloride and 150 ml of chloroform is placed in a 1 liter flask and cooled to 10° C. At 10° to 15° C. and over a period of 35 minutes, a solution of 238 g of 2,3-dichloro-4-hydroxymethylthiophene in 350 ml of chloroform is added. After the exothermic reaction has subsided, the solution is stirred for 1 hour at 30° C., concentrated under reduced pressure and, after a small amount of triethylamine has been added, purified by distillation at 66° to 69° C./0.2 mbar. The yield is 192 g, equivalent to 70% of theory.

The following compounds may be prepared analogously:

$$Z_n \diagdown \substack{\phantom{x}\\ S}\diagup CH_2-Hal$$

| Substituent on the thiophene ring ($Z_n$) | Hal | b.p./m.p. |
|---|---|---|
| — | Cl | 46° C./0.8 mbar |
| 2-bromo | Cl | 63–68° C./0.27 mbar |
| 2,3-dibromo | Cl | 141–146° C. |
| 2,5-dibromo | Cl | 74–76° C./0.07 mbar |
| 2,3,5-tribromo | Cl | 51–53° C. |
| 2-bromo | Br | 88–90° C./0.93 mbar |
| 2-chloro | Cl | 51–53° C./0.33 mbar |
| 2,3-dichloro | Br | 58–60° C./0.13 mbar |
| 2-chloro | Br | 61–62° C./0.53 mbar |

The following examples illustrate the manufacture of the thienylmethyl-thiophosphoric acid esters of the formula I according to the invention.

EXAMPLE 1

0.05 mole of 2,3-dichloro-4-chloromethylthiophene and 100 ml of acetonitrile are placed in a reactor. A solution of 0.05 mole of the dimethylammonium salt of O-ethyl-S-isobutyl-dithiophosphoric acid in 100 ml of acetonitrile is then added. After the mixture has been stirred for 2 hours at room temperature, it is heated at 50° C. for 2 hours, the solvent is then removed, the residue is taken up in ether, and the ether phase is extracted by shaking with water, dried and concentrated. There is obtained 13.7 g (72% of theory) of O-ethyl-S-isobutyl-S-(2,3-dichlorothienyl-4-methyl)-dithiophosphate. The slightly contaminated sample is passed through a silica gel column; $n_D^{25}$: 1.5712.

Analysis: theory: C 34.8, H 4.5, S 25.3, Cl 18.7, P 8.2: found: C 35.0, H 4.5, S 25.1, Cl 19.1, P 7.7.

EXAMPLE 2

0.035 mole of 2,5-dibromo-3-chloromethylthiophene and a solution of 0.037 mole of the dimethylammonium salt of O-ethyl-S-n-propyldithiophosphoric acid in 200 ml of tetrahydrofuran are reacted as in Example 1. It is not necessary to purify the reaction product. There is obtained 12.9 g (82% of theory) of O-ethyl-S-n-propyl-S-(2,5-dibromothienyl-4-methyl)-dithiophosphate; $n_D^{25}$: 1.5987.

Analysis: theory: C 26.4, H 3.3, S 21.2, Br 35.2, P 6.8: found: C 26.9, H 3.4, S 21.2, Br 36.0, P 6.6.

The following compounds may be synthesized analogously:

$$Z_n \diagdown \substack{\phantom{x}\\ S}\diagup CH_2-S-\underset{\underset{YR^2}{|}}{\overset{\overset{X}{\|}}{P}}-OC_2H_5$$

$$R^3 = Z_n \diagdown \substack{\phantom{x}\\ S}\diagup$$

| No. | $R^3$ | $R^2$ | X | Y | $n_D^{25}$ |
|---|---|---|---|---|---|
| 3 | thienyl | sec-$C_4H_9$ | O | S | 1.5591 |
| 4 | thienyl | i-$C_3H_7$ | O | —NH— | 1.5441 |
| 5 | thienyl | i-$C_4H_9$ | O | S | 1.5596 |
| 6 | thienyl | i-$C_3H_7$ | O | S | 1.5661 |
| 7 | thienyl | $CH_3$ | O | S | 1.5818 |
| 8 | 2,3-dichlorothienyl | n-$C_3H_7$ | O | S | 1.5703 |

-continued

General structure:

$Z_n$-(thiophene)-$CH_2$-S-P(=X)(OC$_2$H$_5$)(YR$^2$)

$R^3$ = $Z_n$-(thiophene)

| No. | $R^3$ substituents | $R^2$ | X | Y | $n_D^{25}$ |
|---|---|---|---|---|---|
| 9 | Cl, Cl (dichlorothiophene) | sec-$C_4H_9$ | O | S | ./. |
| 10 | Cl, Cl | i-$C_4H_9$ | O | S | 1.5712 |
| 11 | Br, Br, Br (tribromothiophene) | i-$C_4H_9$ | O | S | 1.6063 |
| 12 | Br, Br, Br | sec-$C_4H_9$ | O | S | 1.6067 |
| 13 | Br, Br, Br | n-$C_3H_7$ | O | S | 1.6121 |
| 14 | Br, Br | sec-$C_4H_9$ | O | S | 1.5934 |
| 15 | Br, Br | i-$C_4H_9$ | O | S | 1.5883 |
| 16 | Br, Br | n-$C_3H_7$ | O | S | 1.5987 |
| 17 | Br (monobromothiophene) | i-$C_4H_9$ | O | S | 1.5724 |
| 18 | Br | n-$C_3H_7$ | O | S | 1.5859 |
| 19 | Cl | sec-$C_4H_9$ | O | S | 1.5632 |
| 20 | Cl | i-$C_4H_9$ | O | S | 1.5643 |
| 21 | Br, Br | i-$C_3H_7$ | O | S | 1.6018 |
| 22 | Br, Br | i-$C_4H_9$ | O | S | 1.5888 |
| 23 | Br, Br | sec-$C_4H_9$ | O | S | 1.5968 |
| 24 | Br | sec-$C_4H_9$ | O | S | |
| 25 | Cl | i-$C_3H_7$ | O | S | |

The compounds according to the invention are suitable for effectively combating injurious or troublesome articulata from the class of insects, Arachnida and Nemathelminthes.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebrana, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephala, Cheimatobia brumata, Hibernia defoliaria, Bupalus piniarus, Hyphantria cunea, Agrotis segetum, Agrotis ypsilon, Barathra brassicae, Cirphis unipuncta, Prodenia litura, Laphygma exigua, Panolis flammea, Earias insulana, Plusia gamma, Alabama argillacea, Lymantria dispar., Lymantria monocha, Pieris brassicae,* and *Aporia crataegi;* examples from the Coleoptera order are *Blitophaga undata, Melanotus communis, Limonius californicus, Agriotes lineatus, Agricotes obscurus, Agrilus sinuatus, Meligethes aeneus, Atomaria linearis, Epilachna varivestris, Phyllopertha horticola, Popillia japonica, Melolontha melolontha, Melolontha hippocastani, Amphimallus solstitialis, Crioceris asparagi, Lema malanopus, Leptinotarsa decemlineata, Phaedon cochleariae, Phyllotreta nemorum, Chaetocnema tibialis, Phylloides chrysocephala,* Diabrotica 12-punctata, *Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;* examples from the Diptera order are *Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae,* and *Pegomya hyoscyami;* examples from the Hymenoptera order are *Athalia rosae, Haplocampa minuta, Monomorium pharaonis, Solenopsis geminata,* and *Atta sexdens;* examples from the Heteroptera order are *Nezara viridula, Eurygaster integriceps, Blissus leucopterus, Dys-*

*dercus cingulatus, Dysdercus intermedius, Piesma quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii;* an example from the Isoptera order is *Reticulitermes lucifugus.*

Examples of mites and ticks (Acarina) belonging to the Arachnida class are *Tetranychus telarius, Tetranychus atlanticus, Tetranychus pacificus, Paratetranychus pilosus, Bryobia praetiosa, Ixodes ricinus. Ornithodorus moubata, Ablyomma americanum, Dermacentor silvarum,* and *Boophilus microplus.*

Examples from the Nemathelminthes class are root-knot nematodes, e.g., *Meloidogyne incognita, Meloidogyne hapla,* and *Meloidogyne javanica,* cyst-forming nematodes, e.g., *Heterodera rostochiensis, Heterodera schachtii, Heterodera avenae, Heterodera glycines,* and *Heterodera trifolii,* and stem and leaf eelworms, e.g., *Ditylenchus dipsaci, Ditylenchus destructor, Pratylenchus neglectus, Pratylenchus penetrans, Pratylenchus goodeyi, Paratylenchus curvitatus* and *Tylenchorhynchus dubius, Tylenchorhynchus claytoni, Rotylenchus robustus, Heliocotylenchus multicinctus, Radopholus similis, Belonolaimus longicaudatus, Longidorus elongatus,* and *Trichodorus primitivus.*

The compounds according to the invention may be successfully employed as pesticides for crop protection, and in the hygiene, stores protection and verterinary sectors.

The active ingredients may be applied as such, in the form of formulations, or of ready-to-use application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The form of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such a kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations generally contain from 0.1 to 95, and preferably 0.5 to 90, % by weight of active ingredient.

The amount of active ingredient in the ready-to-use formulations may vary within a wide range; it is generally from 0.0001 to 10%, preferably from 0.01 to 1%.

The active ingredients may also be successfully used in the ultra-low volume method, where it is possible to apply formulations containing more than 95% of active ingredient, or even the 100% active ingredient.

Examples of formulations are given below.

I. 3 parts by weight of O-ethyl-S-isobutyl-S-(2,3-dichlorothienyl-4-methyl)-dithiophosphate is intimately mixed with 97 parts by weight of particulate kaolin. A dust is obtained containing 3% by weight of the active ingredient.

II. 30 parts by weight of O-ethyl-S-n-propyl-S-(2,5-dibromothienyl-4-methyl)-dithiophosphate is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 20 parts by weight of O-ethyl-S-sec-butyl-S-(2,5-dibromothienyl-4-methyl)-dithiophosphate is dissolved in a mixture consisting of 80 parts by weight of xylene, 10 parts by weight of the adduct of 8 to 10 moles of ethylene oxide to 1 mole of oleic acid-N- monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

IV. 20 parts by weight of O-methyl-S-isobutyl-S-(2-chlorothienyl-4-methyl)-dithiophosphate is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and finely distributing it therein, an aqueous dispersion is obtained containing 0.02% by weight of the active ingredient.

There may be added to the individual active ingredients or mixtures thereof (if desired, immediately before use (tankmix)) oils of various types, herbicides, fungicides, other insecticides, and bactericides. These agents may be added to the active ingredients according to the invention in a weight ratio of from 1:10 to 10:1.

Examples of active ingredients which may be admixed are as follows:

1,2-dibromo-3-chloropropane, 1,3-dichloropropane, 1,3-dichloropropene+1,2-dichloropropane, 1,2-dibromoethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propionaldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N'N'-dimethylformamidine, tetrachlorothiophene, O,O-dimethyl-O-(p-nitrophenyl)-phosphorothioate, O,O-diethyl-O-(p-nitrophenyl)-phosphorothioate, O-ethyl-O-(p-nitrophenyl)-phenylphosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethyl-phosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl] -phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethyl-S-(2-ethylsulfynylethyl)-phosphorothioate, O,O-diethyl-S-(2-ethylthioethyl)-phosphorodithioate, O,O-dimethyl-S-(2-ethylsulfynylethyl)-phosphorothioate, O,O-diethylthiophosphoryliminophenyl-acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5-onyl-(4)-methyl]-phosphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[2-isopropyl-4-methylpyrimidinyl-(6)]-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoroamidothioate, O,S-dimethyl-N-acetylphosphoramidothioate, α-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide, pyrethrins, DL-2-allyl-3-methyl-cyclopenten-(2)-on-(1)-yl-(4)-DL-cis,trans-chrysanthemate, 5-benzylfuryl-(3)-methyl-DL-cis,trans-chrysanthemate, 3-phenoxybenzyl(+)-cis,trans-2,2-dimethyl-3-(2,2-dichlorovinyl)-cyclopropane carboxylate, α-cyano-3-phenoxybenzyl-± )-cis,trans-2,2-dimethyl-3-(2,2-dichlorovinyl)-cyclopropane carboxylate, (s)-cyano-3-phenoxybenzyl-cis(1R,3R)-2,2-dimethyl-3-(2,2-dibromovinyl)-cyclopropane carboxylate, 3,4,5,6-tetrahydrophthalimidoethyl-DL-cis,trans-chrysanthemate, 2-methyl-5-(2-propynyl)-3-furylmethyl-chrysanthemate, and α-cyano-3-phenoxybenzyl-α-isopropyl-4-chlorophenylacetate.

The following experiments demonstrate the biological action. The agents used for comparison purposes are O,O-dimethyl-S-(N-methylcarbamoylmethyl)-phosphorodithioate (I) disclosed in German Pat. No. 819,998 and O,O-diethyl-S-(thienyl-4-methyl)-dithiophosphate (II) and O,O-diethyl-S-(2,3-dichlorothienyl-4-methyl)-dithiophosphate (III) disclosed in U.S. Pat. No. 3,205,238. The active ingredients according to the invention are numbered as in the manufacturing examples and as listed in the table above.

EXAMPLE A

Action on spider mites (*Tetranychus telarius*)

Potted bush beans which have developed the second pair of true leaves and are under heavy attack from spider mites (*Tetranychus telarius*) are sprayed from all sides in a spray cabinet with aqueous formulations of the active ingredients. The plants are then kept under greenhouse conditions at from 22° to 24° C. The action is assessed after 6 days.

| Active ingre- | Kill rate (in %) at active ingredient concentrations of | | | |
|---|---|---|---|---|
| dient no. | 0.1% | 0.05% | 0.02% | 0.01% |
| 1 | | 100 | 100 | |
| 2 | | 100 | | |
| 3 | | 100 | | |
| 5 | | 100 | | |
| 9 | | 100 | 100 | 100 |
| 11 | | 100 | | |
| 13 | | 100 | | |
| 14 | | 100 | limit of action | |
| 15 | | 100 | 100 | |
| I | | limit of action | | |
| II | 80 | ineffective | | |
| III | ineffective | | | |

EXAMPLE B

Contact action on mosquito larvae (*Aedes aegypti*)

The active ingredient formulations are added to 200 ml of tapwater; 30 to 40 mosquito larvae in the 4th larval stage are then introduced. The action is determined after 24 hours.

| Active ingre- | Kill rate (in %) at active ingredient concentrations of | | | |
|---|---|---|---|---|
| dient no. | 1 ppm | 0.5 ppm | 0.25 ppm | 0.1 ppm |
| 2 | 100 | 100 | 100 | |
| 9 | 100 | 100 | 100 | |
| 11 | 100 | 100 | 90 | |
| 12 | 100 | 100 | 100 | 80 |
| 13 | 100 | 100 | 90 | |
| 14 | 100 | 100 | 100 | 100 |
| 15 | 100 | 100 | 100 | |
| I | approx. 20 | | | |
| II | ineffective | | | |
| III | ineffective | | | |

EXAMPLE C

Breeding experiment with housefly larvae (*Musca domestica*)

50 g of a culture medium consisting of baker's yeast, dried milk, water and agar is thoroughly mixed, while warm, with the aqueous active ingredient formulations. After the medium has cooled, approx. 0.1 ml of flies' eggs is placed on it and their development is observed for a week.

| Active ingre- | Kill rate (in %) at active ingredient concentrations of | | | |
|---|---|---|---|---|
| dient no. | 50 ppm | 25 ppm | 10 ppm | 5 ppm |
| 1 | | 100 | 80 | |
| 2 | | 100 | 100 | 100 |
| 9 | | 100 | 100 | |
| 11 | | 100 | 80 | |
| 12 | | 100 | 60 | |
| 13 | | 100 | | |
| 14 | | 100 | 100 | 100 |
| 15 | | 100 | 100 | 100 |
| II | ineffective | | | |
| III | ineffective | | | |

EXAMPLE D

Contact action on cotton stainers (*Dysdercus intermedius*)

Petri dishes 10 cm in diameter are lined with 1 ml of acetonic solutions of the active ingredients.

After the solvent has evaporated, 20 larvae of the penultimate stage are placed in the dishes, and the action is determined after 24 hours.

| Active ingre- | Kill rate (in %) at active ingredient amounts per dish of | | | |
|---|---|---|---|---|
| dient no. | 1 mg | 0.1 mg | 0.05 mg | 0.02 mg |
| 3 | | 100 | 100 | 80 |
| 5 | | 100 | 100 | 70 |
| 6 | | 100 | 85 | |
| II | ineffective | | | |
| III | ineffective | | | |

EXAMPLE E

Contact action on aphids (*Aphis fabae*); spray experiment

Potted bean plants (*Vicia faba*) heavily infected with aphid colonies are sprayed to runoff in a spray chamber with aqueous formulations of the active ingredient.

The kill rate is determined after 24 hours.

| Active ingre- | Kill rate (in %) at active ingredient concentrations of | | | |
|---|---|---|---|---|
| dient no. | 0.1% | 0.5% | 0.02% | 0.01% |
| 1 | | 100 | 90 | |
| 5 | | 100 | 100 | 80 |
| I | ineffective | | | |
| II | | ineffective | | |

EXAMPLE F

Action on root-knot nematodes (*Meloidogyne incognita*)

Young tomato plants are planted in 500 g of compost heavily infested with root-knot nematodes. Treatment with the aqueous active ingredient formulations is effected after 3 days by pouring 30 ml of formulation onto the soil.

After 6 to 8 weeks root-knot formation is assessed.

| Active ingre-dient no. | Active ingredient concentration (%) |
|---|---|
| 2 | 0.025 limit of action |
| 9 | 0.05 no root-knot formation |
| I | 0.1 ineffective |
| II | 0.1 ineffective |

We claim:

1. A thienylmethyl-thiophosphoric acid ester of the formula

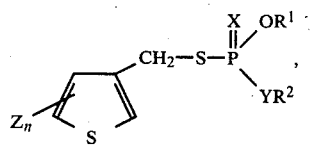

where $R^1$ denotes methyl or ethyl, $R^2$ is linear or branched alkyl of a maximum of 5 carbon atoms, X denotes oxygen or sulfur, Y denotes sulfur, Z denotes halogen, and n denotes one of the integers 0, 1, 2 and 3.

2. O-ethyl-S-n-propyl-S-(2,5-dibromothienyl-4-methyl)-dithiophosphate.

3. O-ethyl-S-isobutyl-S-(2,3-dichlorothienyl-4-methyl)-dithiophosphate.

4. A pesticide comprising a solid or liquid carrier and at least one thienylmethyl-thiophosphoric acid ester of the formula I.

5. A process for combating pests and troublesome articulata, wherein a thienylmethyl-thiophosphoric acid ester of the formula I is allowed to act on the pests or their habitat.

* * * * *